United States Patent [19]

Meredith

[11] 3,937,703

[45] Feb. 10, 1976

[54] PREPARATION OF RDX

[75] Inventor: Joseph A. Meredith, Bluff City, Tenn.

[73] Assignee: The United States of America as represented by the Secretary of the Army, Washington, D.C.

[22] Filed: Nov. 8, 1974

[21] Appl. No.: 522,153

[52] U.S. Cl. .......................................... 260/248 NS
[51] Int. Cl.² ..................................... C07D 251/54
[58] Field of Search ............................. 260/248 NS

[56] References Cited
UNITED STATES PATENTS

| | | | |
|---|---|---|---|
| 2,559,835 | 7/1951 | Zerner et al. | 260/248 |
| 2,568,620 | 9/1951 | Gresham et al. | 260/248 |
| 3,178,430 | 4/1965 | Thatcher | 260/248 |

Primary Examiner—John M. Ford
Attorney, Agent, or Firm—Nathan Edelberg; Robert P. Gibson; A. Victor Erkkila

[57] ABSTRACT

RDX is produced by reacting formaldehyde and an alkyl nitrile RCN, wherein R is an alkyl group of 1 to 3 carbon atoms, in the absence of added solvents, to form a 1,3,5-triacylhexahydro-s-triazine and subjecting the latter, without separation thereof from the reaction mixture, to nitrolysis by contact with concentrated nitric acid to form RDX.

5 Claims, No Drawings

PREPARATION OF RDX

BACKGROUND OF THE INVENTION

RDX (1,3,5-trinitrohexahydro-s-triazine) is usually manufactured industrially by nitrolysis of hexamethylenetetramine with concentrated nitric acid. This conventional process has the disadvantage that a substantial amount of HMX (cyclotetramethylenetetranitramine) is formed as a by-product, which can exist in several polymorphic forms possessing high impact sensitivity and, unless completely removed, would increase the impact sensitivity of the RDX significantly.

U.S. Pat. No. 3,178,430 discloses a process for preparing RDX without the concurrent production of HMX by reacting a 1,3,5-triacylhexahydro-s-triazine with concentrated nitric acid. As disclosed in the patent, the 1,3,5-triacylhexahydro-s-triazine intermediate, which was reacted with the nitric acid, was previously prepared by the method of the *Journal of the American Chemical Society*, Vol. 74, pages 5524–5(1952), wherein formaldehyde and the nitrile were reacted in the presence of carbon tetrachloride or other solvents, and the s-triazine formed was separated from the reaction mixture and purified by recrystallization from a solvent.

SUMMARY OF THE INVENTION

An object of the present invention is to provide a process for the preparation of RDX by nitrolysis of the triazine intermediate without isolation thereof from the reaction mixture in which it is formed from formaldehyde and a nitrile.

Other objects will become apparent as the invention is further described.

In accordance with the process of the present invention, RDX is obtained in simple manner by reacting a formaldehyde, such as trioxane and paraformaldehyde, with a nitrile of the general formula RCN, wherein R is an alkyl group containing 1–3 carbon atoms, in the absence of added solvents to produce the corresponding 1,3,5-triacylhexahydro-s-triazine, and thereafter reacting the latter in situ, i.e., without separation thereof from the reaction mixture, with concentrated nitric acid.

The process of the present invention is relatively simple and efficient, produces RDX of high purity free from HMX, and eliminates the simmer purification for the destruction of linear by-products associated with the aforesaid conventional industrial RDX process.

DESCRIPTION OF THE PREFERRED EMBODIMENTS

The following examples serve to illustrate specific embodiments of the method of carrying out the process of the present invention.

EXAMPLE 1

13.8 Grams (0.25 mol) of propionitrile and a catalytic amount (0.65 gram) of concentrated sulfuric acid were mixed and heated to gentle reflux of the nitrile in a glass flask provided with a dropping funnel, air driven agitator and reflux condenser. A solution of 15 grams (0.5 mol) of formaldehyde as trioxane in 13.8 grams (0.25 mol) of propionitrile was added to the flask contents during about 30 minutes at such a rate as to maintain the reflux. When the addition was about one-third complete, the triazine compound began to separate as a white solid; and when the addition was complete, the slurry was quite heavy with solids, and if allowed to cool, the slurry became a very viscous semisolid. After the addition of the propionitrile-trioxane solution was complete, the slurry was added slowly portionwise to about 10 volumes of 99% nitric acid, which was agitated in a glass flask cooled in an ice bath. The agitated reaction mixture was held for an additional 15 minutes with ice bath cooling, allowed to warm to ambient temperature for 15 minutes and then heated to about 60°C. for 60 minutes. The reaction mixture was then allowed to cool to room temperature and drowned into five volumes of ice water. The precipitated RDX was filtered off, washed with water and dried. The RDX was thus obtained in high purity and 21% theory yield, based on the propionitrile.

EXAMPLE 2

The procedure described in example 1 for preparing the slurry of the 1,3,5-tripropionylhexahydro-s-triazine intermediate was repeated using the following amounts of reactants:

2.12 grams (0.04 mol) propionitrile
1.15 grams (0.04 mol) formaldehyde as trioxane
0.05 gram (0.0005 mol) concentrated sulfuric acid.

The slurry was added during 8 minutes to 50 ml of 99% nitric acid cooled in an ice bath. The agitated reaction mixture was maintained in the ice bath for 15 minutes, allowed to warm to ambient temperature for 15 minutes and then heated to about 60°C. for 60 minutes. The reaction mixture was poured over 200 grams of ice, and the precipitated RDX was filtered off, washed with water and dried. The RDX was thus obtained in 99+% purity and 31% of theory yield, based on propionitrile.

In the foregoing example the ratio of $HNO_3$ volume to slurry weight was 15/1 and the total nitration reaction time was 90 minutes. When the foregoing example was repeated except that the $HNO_3$/slurry ratios were 7.5/1 and 10/1, the RDX was obtained in the same yield and quality. Lower yields of RDX were obtained when in the foregoing example the $HNO_3$/slurry ratio was 15/1 but the total nitration reaction time was considerably shorter (about 25 minutes) or longer (150 minutes).

The acid catalyzed reaction of nitriles and formaldehyde in the absence of solvents other than the nitrile to produce the corresponding 1,3,5-triacylhexahydro-s-triazines is known (e.g. *J. Am. Chem. Soc.* 70, 3079 (1948), U.S. Pat. No. 2,559,835). The reported yield of the tripropionyl derivative obtained from propionitrile is about 47% of theory based on propionitrile (see also *J. Am. Chem. Soc.* 74, 5524 (1952)). Further, the yields of RDX obtained by nitrolysis of 1,3,5-tripropionylhexahydro-s-triazine with concentrated nitric acid as reported in U.S. Pat. No. 3,178,430 range from about 20% to about 75% of theory. It is evident from the foregoing that the present invention, by effecting the nitrolysis of the triazine intermediate without isolation and purificaton thereof from the reaction mixture in which it is formed, provides a simpler process, which can produce RDX in high purity and without loss of RDX yield from the initial nitrile. Further, in the present process, by eliminating the use of added solvents in the reaction of the nitrile and formaldehyde to form the triazine intermediate, the by-product contaminants are the respective carboxylic acid of the nitrile and/or derivatives of the nitrile and formaldehyde. These by-product contaminants are water soluble whereas the RDX is water soluble, so that the RDX can be isolated in high purity by diluting the nitration mixture with water and separating the RDX from the aqueous mixture containing the dissolved impurities, e.g. by filtration.

In similar manner nitriles of the foregoing general formula RCN other than propionitrile, e.g. acetonitrile and butyronitrile, can be reacted with formaldehyde, such as trioxane and paraformaldehyde, and the resulting 1,3,5-triacylhexahydro-s-triazine nitrolyzed in situ with concentrated nitric acid.

The reaction conditions for producing the 1,3,5-triacylhexahydro-s-triazines by acid catalyzed condensation of formaldehyde, such as paraformaldehyde and trioxane, with nitriles of the foregoing general formula in the absence of added solvents, as well as the conditions for the nitrolysis of the triazine derivative with concentrated nitric acid, are known and are generally suitable for use in the present process with the exception that in the nitration step of the present process the nitric acid is contacted with the triazine intermediate without isolation of the latter from the reaction slurry in which it is formed. Thus, for example, in the formation of the triazine intermediate, the amount of nitrile employed can be about 1 mol or more per mol of formaldehyde. In the nitrolysis step the concentration of the nitric acid used is preferably between 90 and 100% and especially 98–100%, and the ratio of the volume of the nitric acid to the weight of the slurry containing the triazine intermediate, is generally at least about 5 parts of nitric acid per part of reaction slurry. The nitric acid and triazine slurry are preferably mixed at about 0°–20°C, prior to heating to a temperature at which the nitrolysis rate is significant, i.e. at least about 40°C. and up to the reflux temperature of the nitric acid, namely 80°–85°C. The yield of RDX produced is also affected by the duration of contact of the nitric acid with the triazine slurry in that a prolonged contact period generally tends to promote the production of by-products at the expense of RDX yield while an excessively short contact period results in an incomplete reaction and a low yield of RDX.

The foregoing disclosure is merely illustrative of the principles of this invention and is not to be interpreted in a limiting sense. I wish it to be understood that I do not desire to be limited to exact details of construction shown and described, because obvious modifications will occur to a person skilled in the art.

I claim:

1. A process for preparing 1,3,5-trinitrohexahydro-s-triazine, which comprises reacting formaldehyde with a nitrile of the general formula RCN, wherein R is an alkyl group of 1 to 3 carbon atoms, in the absence of added solvents to produce the corresponding 1,3,5-triacylhexahydro-s-triazine, and contacting the resulting reaction mixture containing said triazine with concentrated nitric acid at a temperature sufficient to effect nitrolysis of said triazine to form 1,3,5-trinitrohexahydro-s-triazine.

2. The process of claim 1, wherein the nitrile is acetonitrile.

3. The process of claim 1, wherein the nitrile is propionitrile.

4. The process of claim 3, wherein about equimolecular proportions of propionitrile and formaldehyde as trioxane or paraformaldehyde are reacted in the presence of a catalytic amount of concentrated sulfuric acid to form 1,3,5-tripropionylhexahydro-s-triazine, and the resulting reaction mixture is contacted with 98–100% nitric acid to effect said nitrolysis.

5. The process of claim 4, wherein one part by weight of the resulting reaction mixture containing the 1,3,5-tripropionylhexahydro-s-triazine is contacted with about from 7.5 to 15 parts by volume of 98–100% nitric acid to effect said nitrolysis.

* * * * *